United States Patent [19]

Chan et al.

[11] Patent Number: 5,190,847

[45] Date of Patent: Mar. 2, 1993

[54] PHOTOGRAPHIC SILVER HALIDE MATERIALS CONTAINING ARYL HYDRAZIDES

[75] Inventors: Dominic M. Chan, Wilmington, Del.; Reinhold Rüger, Rodermark, Fed. Rep. of Germany

[73] Assignee: E. I. du Pont de Nemours and Company, Wilmington, Del.

[21] Appl. No.: 661,596

[22] Filed: Feb. 20, 1991

[30] Foreign Application Priority Data

Feb. 26, 1990 [DE] Fed. Rep. of Germany ....... 4006032

[51] Int. Cl.$^5$ ................................................ G03C 1/06
[52] U.S. Cl. ...................................... 430/264; 430/598
[58] Field of Search ............................... 430/264, 598

[56] References Cited

U.S. PATENT DOCUMENTS

| | | | |
|---|---|---|---|
| 3,385,831 | 6/1968 | Honig et al. | 96/109 |
| 4,224,401 | 9/1980 | Takada et al. | 96/66 R |
| 4,937,160 | 6/1990 | Ruger | 430/264 |
| 5,013,844 | 5/1991 | Ruger | 546/347 |
| 5,028,510 | 7/1991 | Okamura et al. | 430/264 |
| 5,061,594 | 10/1991 | Okamura et al. | 430/264 |
| 5,130,480 | 7/1992 | Ruger | 564/151 |

FOREIGN PATENT DOCUMENTS

| | | |
|---|---|---|
| 0253665 | 1/1988 | European Pat. Off. |
| 62-275247 | 11/1987 | Japan . |
| 1-090444 | 4/1989 | Japan ................ 430/598 |
| 2-090146 | 3/1990 | Japan ................ 430/598 |
| 702162 | 1/1954 | United Kingdom . |

OTHER PUBLICATIONS

Research Disclosure 23510, Anonymous, Nov. 1983.
Katritsky, Alan R., et al., Chemical Abstracts, vol. 99:158195W.

Primary Examiner—Charles L. Bowers, Jr.
Assistant Examiner—Thomas R. Neville

[57] ABSTRACT

Photographic silver halide materials containing aryl hydrazides as defined and novel aryl hydrazides with a cationic group in the acyl radical enables the preparation of photographic materials that can be developed rapidly to ultrahigh contrast at a relatively low pH value. The photographic materials are useful in reprography, particularly screening for halftone images.

3 Claims, No Drawings

PHOTOGRAPHIC SILVER HALIDE MATERIALS CONTAINING ARYL HYDRAZIDES

DESCRIPTION

1. Technical Field

The invention relates to photographic silver halide materials containing certain aryl hydrazides, preferably for rapid processing, for producing images with ultrahigh contrast, and to novel aryl hydrazides for use in such photographic materials.

2. Background of the Invention

Photographic silver halide systems with ultrahigh contrast are used, for example, in reprography for producing screened images for halftone photographic records, for phototypesetting technology, for line photographs, and for photomasks. The expression "ultrahigh" means that the contrast is higher than can be expected, if it is assumed that each individual emulsion grain is exposed and developed independently of its neighbors. Such systems utilize, for example, effects in which the development of a grain initiates the development of a neighboring grain, even if the latter has not been sufficiently exposed to be developable on its own ("infectious development").

The so-called lithographic systems have long been known. These consist of films, in most of which the greatest proportion of the silver halide is the chloride, and of associated developers characterized by a relatively high pH value, a low sulfite content, and the absence of superadditive developer compounds. Consequently, the light sensitivity of the films and their development rate are relatively limited, and considerable effort is required to maintain developer activity constant over a longer period of time.

These disadvantages have been mitigated by recently introduced systems, in which the photographic material is developed in the presence of certain hydrazine compounds. Research Disclosure 23510 (November 1983) summarizes the extensive literature on this subject. According to this disclosure, so-called activated hydrazine compounds are predominantly used, as can be represented by the generic formula

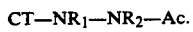

CT—NR$_1$—NR$_2$—Ac.

In this formula, CT is a tertiary carbon, mostly as a component of an aromatic ring system, such as, phenyl; R$_1$ and R$_2$ are radicals that can be split off by alkali and Ac is an activating group. The hydrazine compounds are usually added to the light sensitive layer systems. The effect of the alkaline developer solution interacting with oxidation products generated from the developer compound in the development of the silver halide grains produces free hydrazine compounds that fog neighboring grains. In practice, preferred hydrazine compounds have the activating group linked through carbonyl groups to the hydrazine nitrogen. If CT is a tertiary carbon in an aromatic group, these substances are also designated as aryl hydrazides.

A disadvantage of systems with hydrazine compounds is that development must be conducted at relatively high pH values. Although relevant publications do indeed cite developer pH values in the range of about 9 to 12.5, in practice, however, values above 11.5 are used exclusively, because, otherwise, satisfactory development rate is not achieved, and image quality is inadequate. Hence, the developer solutions are not sufficiently stable for problem-free processing. In particular, despite their high sulfite content, they are very sensitive to oxygen in the air. Also, development behavior changes so much from unavoidable, small variations in the pH value during operation that it is difficult to maintain uniform results over a longer period of time. Other problems are extensive corrosion of the development machines by the highly alkaline developer solutions and disposal of the comparatively highly buffered, exhausted solutions.

EP 02 53 665-41 discloses photographic materials containing hydrazine compounds, in which the activating group is split off in the alkaline developer medium to form a ring structure. These materials can even be developed at pH 11 with satisfactory results. By this means, the above-described disadvantages are indeed lessened; however, there is still a need for further improvement. Furthermore, the aryl hydrazides used therein can be prepared only by multistep syntheses or with mediocre yields.

Although hydrazine compounds have already been shown to be technically superior in many respects for lithographic systems, a need still exists particularly to accelerate further the processing operation, whose duration is determined decisively by development time.

Therefore, an object of this invention is to supply photographic silver halide materials with hydrazine compounds, materials that can be developed comparatively rapidly at relatively low pH values to ultrahigh contrast. Another object is to supply materials of this type, whose development results depend only slightly on pH value. A further object is to supply new hydrazine compounds that are suitable for preparing such materials and that can be prepared with good yields at low cost.

SUMMARY OF THE INVENTION

In accordance with this invention there is provided a photographic material containing an aryl hydrazide for the production of image with ultrahigh contrast comprising a support having therein at least one silver halide emulsion layer, the emulsion, or at least one other auxiliary layer in contact with a silver halide emulsion layer on said support contains a compound of Formula (I)

Ar—NR—NR$_1$—G—X$^+$ $A^-$     (I)

wherein Ar is a substituted phenyl group or another substituted or unsubstituted aryl group, G is the group CO, SO, SO$_2$, phosphonyl, phosphoryl or C=NR$_2$, X$^+$ is a radical containing a cationic group with a quaternary nitrogen atom, R, R$_1$, and R$_2$, which can be the same or different, are hydrogen, alkyl or alkyl sulfinyl groups with one to six carbon atoms, and A$^-$ is an anion, the improvement wherein the quaternary nitrogen atom is included in a substituted or unsubstituted imidazolium, imidazolinium, isoquinolinium, quinolinium group or in a pyridinium group substituted on one or more carbon atoms, with the proviso that sulfoethyl pyridinium is excluded.

DETAILED DESCRIPTION OF THE INVENTION

The radical Ar in Formula (I) can be a substituted phenyl radical or another substituted or unsubstituted aryl radical, for example, a naphthyl, anthryl, or phenanthryl radical.

The substituents on the aromatic ring system of the radical Ar contain preferably groups that are used in the current state of the art to confer on the hydrazine compound certain properties, such as, for example, a specific diffusion capability (ballast groups), or to confer a specific adsorption behavior on the silver halide (adsorption-enhancing groups). Examples of such substituents are straight chain, branched or cyclic alkyl, alkenyl, or alkinyl groups, preferably with one to 20 carbon atoms, that can themselves be substituted further with any of the radicals named in this section, e.g., halogen atoms, cyano, carboxyl, amino, substituted or unsubstituted aryl radicals with six to 14 carbon atoms, alkylamino and acylamino radicals with one to 20 carbon atoms, thiourea radicals and other radicals containing thiocarbonyl groups, alkoxy and aryloxy radicals, aliphatic and aromatic acyloxy radicals, urethane groups, alkyl sulfonyl and aryl sulfonyl, alkyl sulfamido and aryl sulfamido radicals, and radicals of nitrogen-containing or sulfur-containing heterocycles with five to 10 members, such as imidazole, thiazole, benzthiazole, benzimidazole. The cited substituents can be linked to the aryl radical independently of each other or can, themselves being mutually substituted, be linked to a chain. Substituents that increase the electron density of the aromatic ring system by mesomeric or inductive effects work well.

On the basis of the current state of the art, the expert would not expect the invention's compounds with cationic groups in the activating radical to have improved properties, particularly a higher development rate at low pH values. A known comparison test with simple hydrazines (DE 27 25 743 C3, page 14) shows that such a group has no effect at all on the development of contrast. According to DE 11 99 612, an aryl hydrazide, unsubstituted on the aryl radical, with a cationic group in the acyl radical has a strong fogging effect on highly sensitive iodobromide emulsions without affecting contrast. In comparison, the materials of the invention show ultrahigh contrast on appropriate development and no increase in fog on longer storage.

The anion $A^-$ can be a halide anion, for example, a chloride, bromide, or iodide ion, but also a complex inorganic ion, such as sulfate or perchlorate, or a common organic ion, such as, toluene sulfonate or trichloroacetate. Anions of strong acids are preferred. If the hydrazine compound is substituted on a radical with an anionic group, the anion is optionally omitted, because of the formation of an inner salt.

During the work on the invention, new aryl hydrazides were found, as represented by the generic Formula (II):

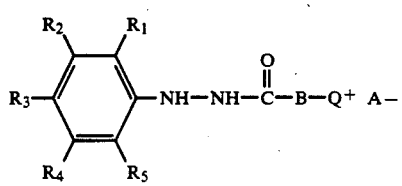

wherein $R_1$ to $R_5$ are radicals, which can be the same or different, at least one of which, however, is not hydrogen, and which are represented by hydrogen, halogen, alkyl, alkoxy, hydroxyalkyl, halogenated alkyl, alkylamino, aliphatic acylamino, with, in each case, one to 20 carbon atoms, cycloalkyl with 5 to 7 carbon atoms, aryl, aryloxy, or aromatic acylamino with, in each case, six to ten carbon atoms, aralkyl or aralkoxy with one to three carbon atoms in the alkylene chain, an aliphatic acylamino radical with one to four carbon atoms and substituted with a phenoxy radical optionally substituted with one or more alkyl radicals with one to ten carbon atoms, a five-member or six-member heterocyclic ring with nitrogen and/or sulfur as heteroatoms, which ring can also be condensed on a benzene ring, or an alkyl or phenyl sulfonamido radical, whereby, in place of two substituents, a saturated or unsaturated ring can also be condensed onto the compound, $Q^+$ is 3-alkyl or 3-alkenyl imidazole-1-yl, optionally substituted further, quinolyl, isoquinolyl optionally substituted, or pyridyl substituted on one or more carbon atoms, with the proviso that sulfoethyl pyridinium is excluded whereby the substituents can be alkyl, alkenyl, amino alkyl, hydroxyalkyl radicals, benzyl, phenyl, phenylmethyl or pyridyl radicals, carboxyl, carbamide, carboxyalkyl, cycloalkyl thioureimido methyl or hydroxyl groups, trialkylammonium ethyl groups, amino, monoalkylamino and dialkylamino groups, N-piperidino groups, N-pyrrolidino groups or also chlorine, the heterocyclic ring can be condensed to a benzene ring, and whereby all alkyl groups of a radical $Q^+$ can be the same or different and/or can be substituted with hydroxyl or sulfonic acid groups, each alkyl group having, however, 12 carbon atoms at most, B is a bridge that can contain one to three methylene groups, an oxygen atom, and —CO—NH— or —NH— groups, or, if it is not directly attached to a quaternary nitrogen, can also consist of a simple bond, whereby the methylene groups and —NH—groups themselves can be substituted with methyl or ethyl groups, $A^-$ is an anion that is omitted if $Q^+$ contains a sulfo group or a carboxyl group.

It is advantageous for the aryl hydrazides to be substituted on the aryl portion or acyl portion of the molecule with radicals that favor adsorption on silver halide. Such radicals are disclosed, for example, in Patent Publications DE 26 35 316, DE 26 35 317, DE 28 51 219, DE 29 13 567, DE 29 41 428, DE 29 42 766, DE 29 51 219, DE 29 52 587, EP 23 780, and EP 1 26 000.

Particularly preferred aryl hydrazides of Formula (II) are substituted on any of the radicals $R_1$ to $R_5$ or $Q^+$ with a radical of the formula $R_6$—X—CS—X'—, whereby one of the groups X and X' is represented by $NR_7$ and the other by $NR_8$, —O— or —S—, and $R_6$, $R_7$, and $R_8$ are represented by hydrogen, alkyl, cycloalkyl, or aryl groups with up to eight carbon atoms.

The following are some examples of the invention's compounds in accordance with Formula (II):

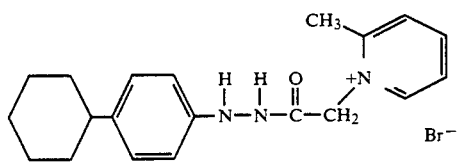 (II-1)
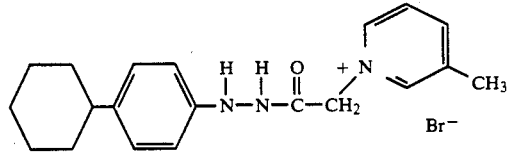 (II-2)
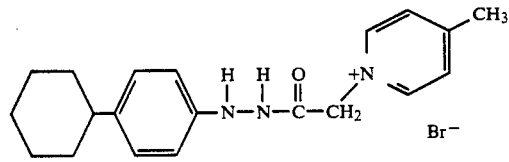 (II-3)
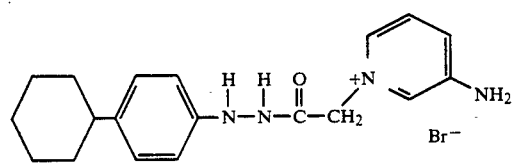 (II-4)
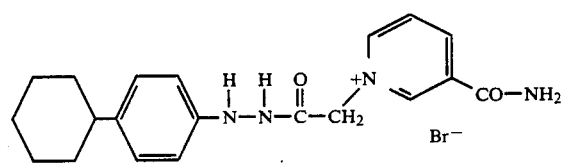 (II-5)
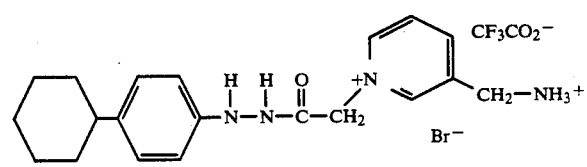 (II-6)
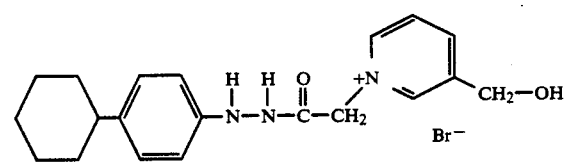 (II-7)
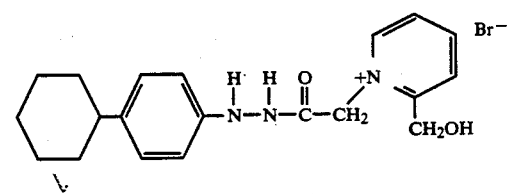 (II-8)
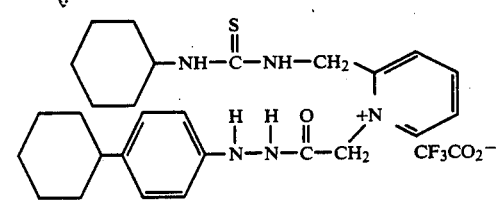 (II-9)

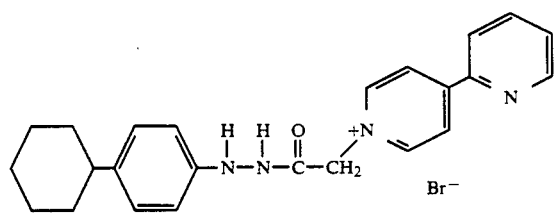
(II-10)
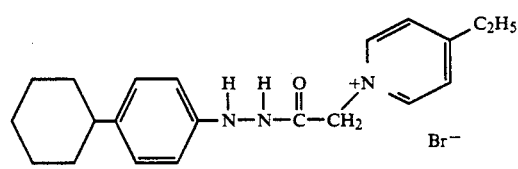
(II-11)
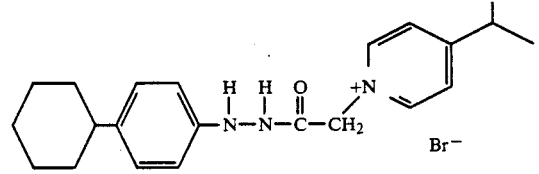
(II-12)
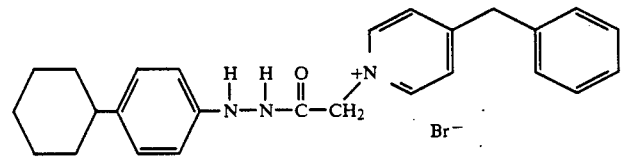
(II-13)
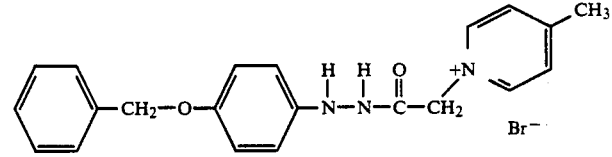
(II-14)
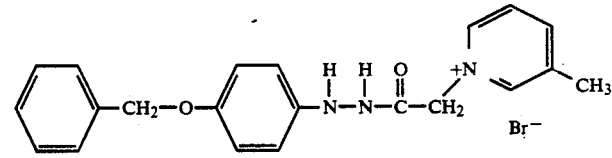
(II-15)
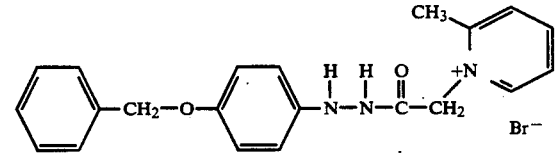
(II-16)
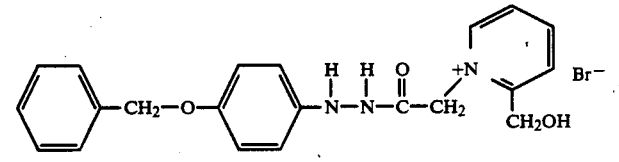
(II-17)
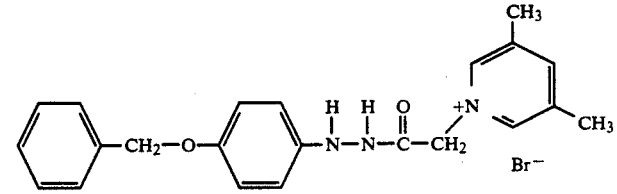
(II-18)

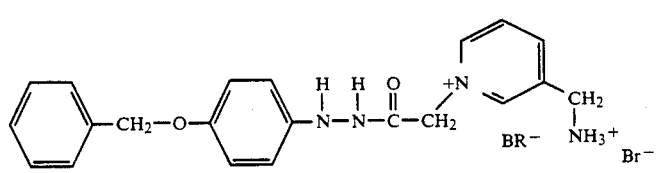
(II-19)
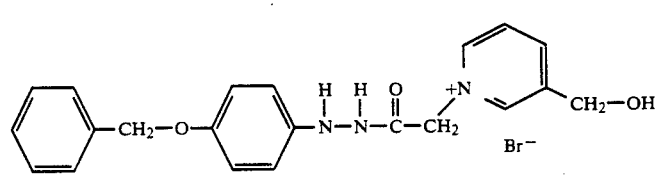
(II-20)
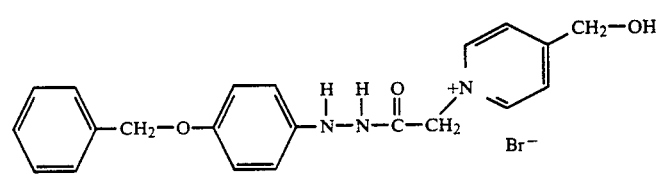
(II-21)
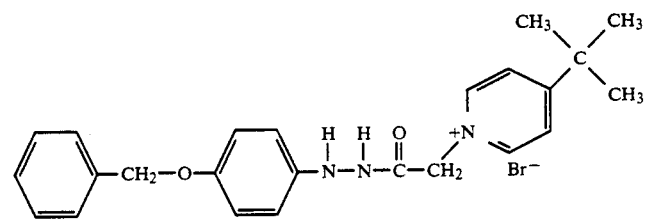
(II-22)
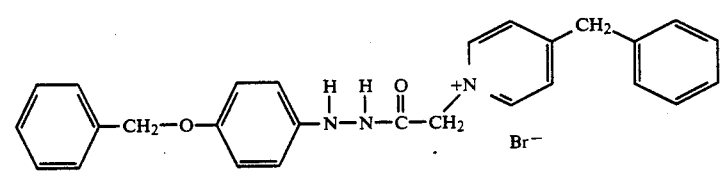
(II-23)
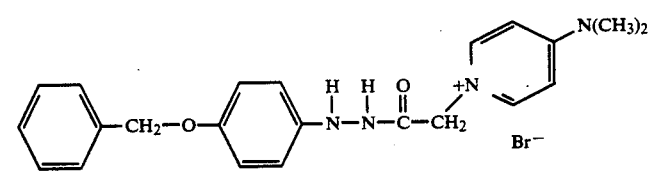
(II-24)
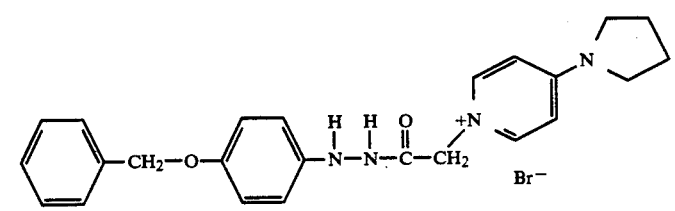
(II-25)
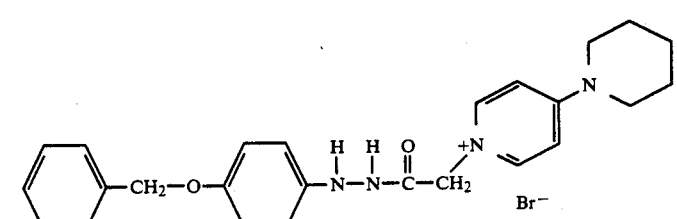
(II-26)

-continued
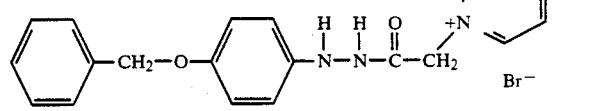 (II-27)
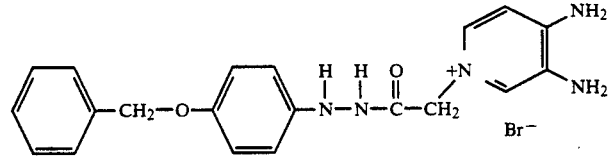 (II-28)
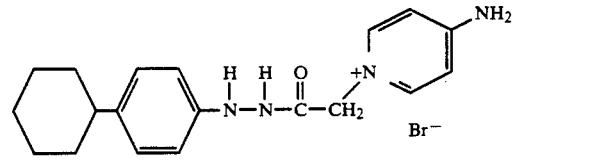 (II-29)
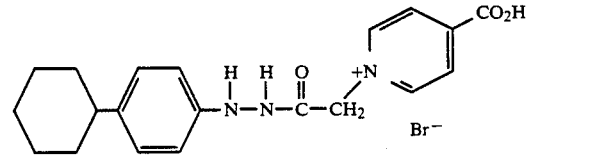 (II-30)
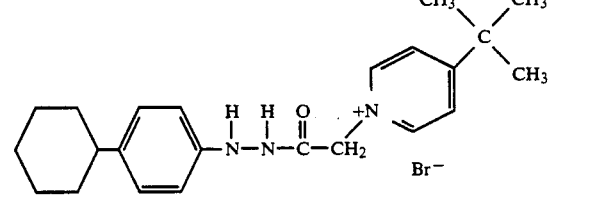 (II-31)
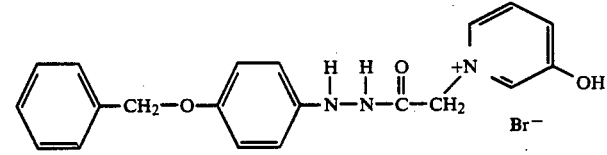 (II-32)
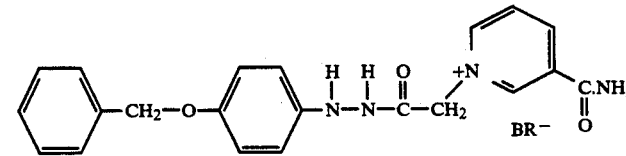 (II-33)
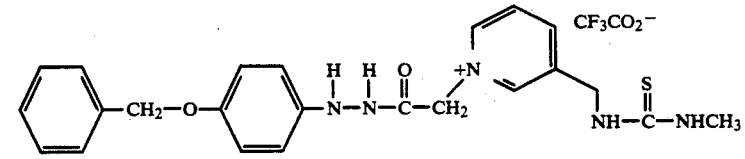 (II-34)
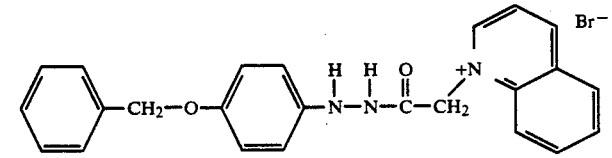 (II-35)

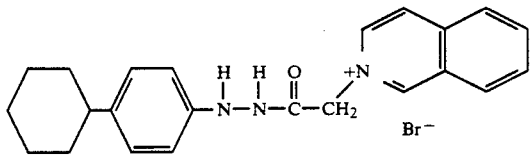
(II-36)
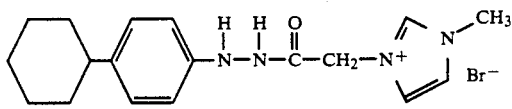
(II-37)
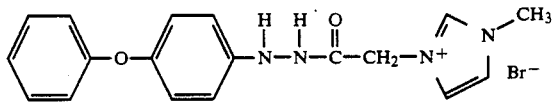
(II-38)
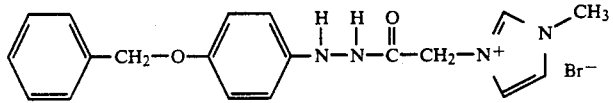
(II-39)
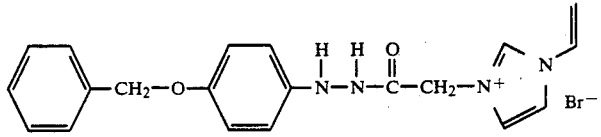
(II-40)
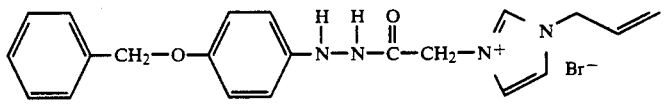
(II-41)
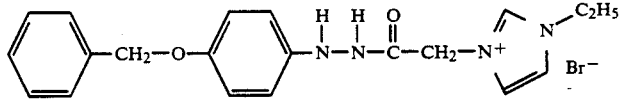
(II-42)
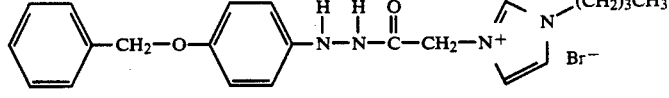
(II-43)
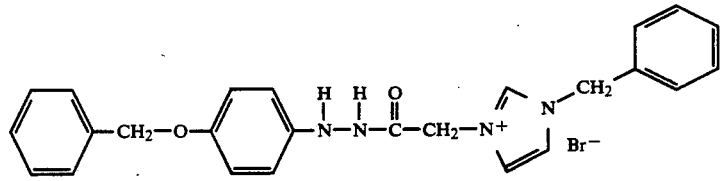
(II-44)
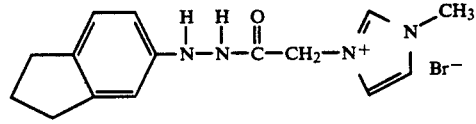
(II-45)
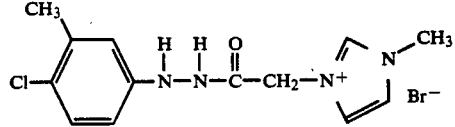
(II-46)
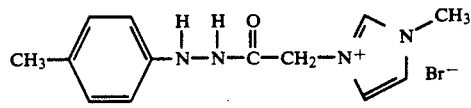
(II-47)

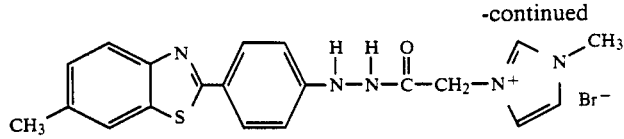 (II-48)
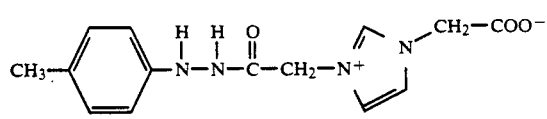 (II-49)
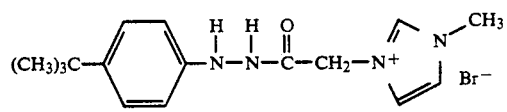 (II-50)
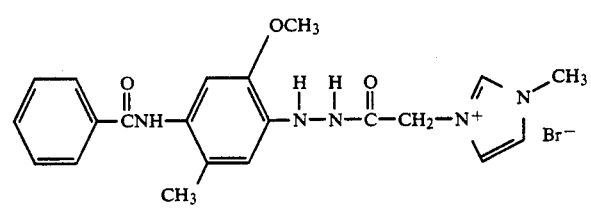 (II-51)
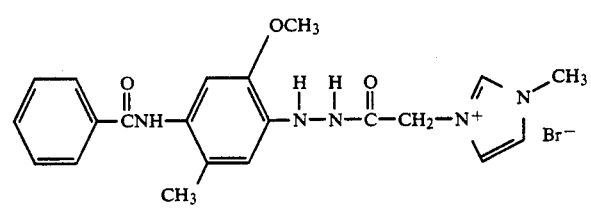 (II-52)
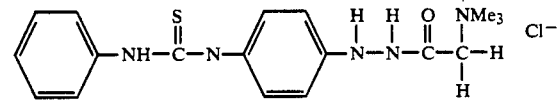 (II-53)
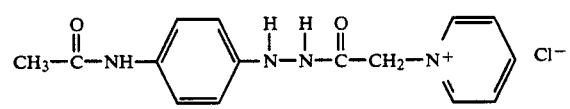 (II-54)
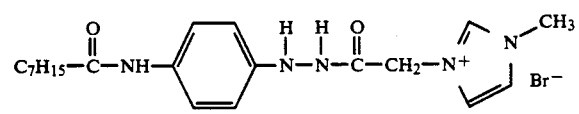 (II-55)
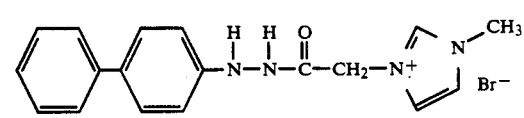 (II-56)
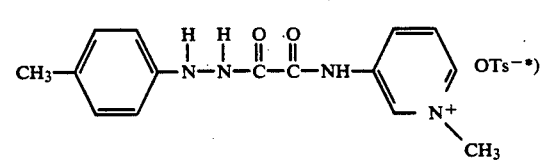 (II-57)
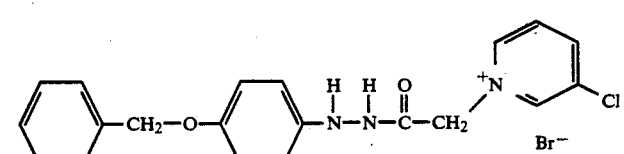 (II-58)
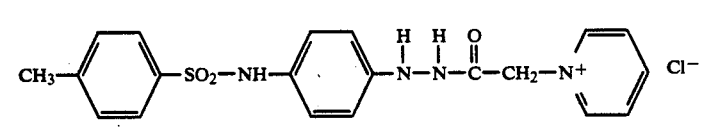 (II-59)
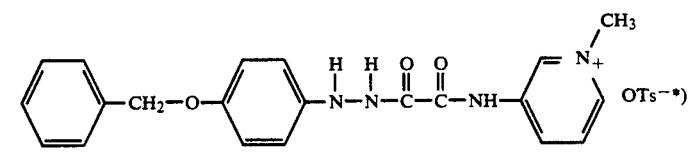

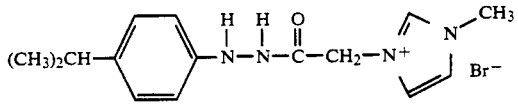

(II-60)

*) p-toluene sulfonate anion

The aryl hydrazides of the invention can be prepared easily by various methods, for example, from equal molar amounts of the aryl hydrazine, the corresponding carboxylic acids and dicyclohexyl carbodiimide (see "Methods of Organic Chemistry" (Houben-Weyl), 4th edition, volume X/2, page 355). Another route to incorporate the aryl radical in the hydrazide goes through quinone monoacyl hydrazones or quinone oxime monoacyl hydrazones (see Houben-Weyl, same volume, page 233). A third possibility is the hydrazinolysis of carboxylic acid esters (Houben-Weyl, same volume, page 360 ff.). The expert knows other synthesis possibilities.

The aryl hydrazines required for the syntheses can be prepared by the methods given in Houben-Weyl, volume X/2, page 169 ff. Diazotization of the corresponding aryl amine followed by reduction of the diazonium compound with tin (II) chloride is particularly suitable (see Houben-Weyl, volume X/2, page 203).

The carboxylic acid esters with a cationic group are synthesized, for example, by alkylation of a tertiary amino compound with a halogenated alkane carboxylic acid ester in acetone or tetrahydrofurane. For example, bromoacetic acid esters are especially suitable. Another possibility is to quaternize a carboxylic acid ester, whose carboxylic acid radical contains a tertiary nitrogen, with an alkylating agent, such as, for example, the methyl ester of toluene sulfonic acid. Another synthesis is described in Example 1.

A particularly preferred embodiment of the invention is photographic silver halide materials containing compounds of generic Formula (II).

The light-sensitive silver halides of the materials of the invention consist of silver chloride, silver bromide, silver chlorobromide, silver bromoiodide, or silver chlorobromoiodide. They can be monodisperse or polydisperse. They can have a uniform composition, but can also have grains with a core-shell structure, as well as mixtures of grains of different composition and grain size distribution. They are prepared with the use of a hydrophilic, colloidal binder, preferably gelatin. Methods for preparing suitable light-sensitive silver halide emulsions are known to the expert and summarized, for example, in Research Disclosure 178 043, Sections I and II.

Silver halide emulsions preferred for the material of the invention are made by controlled double jet precipitation, have cubic grains, and the chloride proportion is less than 50 mole percent.

The grain size of the emulsions is selected for the required sensitivity and can be between 0.1 and 0.7 $\mu$m edge length, the preferred range lying between 0.15 and 0.30 $\mu$m edge length. When the emulsions are prepared, noble metal salts, particularly rhodium or iridium salts, can be present in the usual quantities to improve photographic properties.

The emulsions are sensitized preferably chemically. Suitable methods are sulfur, reduction, and noble metal sensitizations, which can also be used in combinations. In the latter, iridium compounds, for example, can be used.

The emulsions can be sensitized spectrally with conventional sensitizing dyes.

The emulsions can also contain conventional antifoggants. Preferred examples are optionally substituted benzotriazole, 5-nitroindazole and mercury chloride. These agents can be added at any time point in emulsion preparation or can be contained in an auxiliary layer of the photographic material. To improve photographic properties, about one mmole of an iodide per mole silver can be added to the emulsion before or after chemical ripening.

The emulsions can also contain known polymer dispersions to improve, for example, the dimensional stability of the photographic material. Generally, these involve latexes of hydrophobic polymers in an aqueous matrix. Examples of suitable polymer dispersions are disclosed in Research Disclosure 176 043, Section IX B (December 1978).

The light-sensitive layers of the photographic materials can be hardened with a known agent. This hardening agent can be added to the emulsion or applied in an auxiliary layer, for example, a protective overcoating. A preferred hardening agent is hydroxy dichlorotriazine.

The photographic material can contain other additives that are known and customary to produce certain characteristics. Such agents are listed, for example, in Research Disclosure 176 043 in Section V (Clarifiers), XI (Coating Aids), XII (Plasticizers and Slip Agents), and XVI (Matting Agents).

The gelatin content of the emulsions is generally between 50 and 200 grams per mole silver, the range between 70 and 150 grams per mole silver being preferred.

The aryl hydrazides of the invention are preferably incorporated in the emulsion, but can be contained in an auxiliary layer in contact with the emulsion layer. For example, a solution of the aryl hydrazide is added to one of the coating solutions. It is added to the emulsion optionally preferably after chemical ripening, but it can also be added at another time point. A suitable solvent for the aryl hydrazides of the invention is, for example, ethanol. The concentration of the compounds in the film can be varied over a wide range and is governed by, in addition to the effectiveness of the compound, what the expert knows about the functional relation between infectious development and the other components of the film, for example, binder proportion and binder composition, halide composition and emulsion grain size, degree of chemical ripening of the emulsion, and type and amount of stabilization. The expert can easily and accurately coordinate the quantity with the cited parameters. The concentration of the compounds can be in the range between $10^{-5}$ mole per mole silver to $5 \times 10^{-2}$ mole per mole silver, the range between $5 \times 10^{-4}$ and $10^{-2}$ mole per mole silver being preferred.

Developer solutions containing preferred dihydroxy benzenes, such as, hydroquinone, are used for processing the materials of the invention. In addition, developers can contain other developer compounds, including those acting superadditively, such as, 1-phenyl pyrazolidinone or N-methyl-p-aminophenol, and known antifoggants. The preferred sulfite content is above 0.15 mole/liter. Development is conducted preferably in the presence of other materials to increase contrast, such as, for example, alkanolamines or secondary aliphatic or aromatic alcohols. The development temperature is between 15° and 50° C., preferably between 30° and 45° C. The developer solution has a pH value between 9 and 12.5, the range between 10 and 11.5 being preferred. Development time can be from 10 to 500 seconds, depending on developer temperature.

The materials of the invention can be fixed, washed, and dried by known and practiced methods.

INDUSTRIAL APPLICABILITY

The photographic silver halide materials of the invention can be developed at relatively low pH values and in short development times to ultrahigh contrast and outstanding dot quality. They show little fog and little tendency to form black spots, known to the expert as "pepper", in unexposed or slightly exposed areas. The effect of developer pH value on development rate and sensitivity is particularly small in the range of pH 11, so that unavoidably small pH variations in the operation do not noticeably affect the photographic result.

The aryl hydrazides of the invention are more highly effective as nucleating agents, compared to prior art hydrazine compounds, particularly compared to formyl hydrazides with a comparable chemical structure. Therefore, they can be used in smaller quantities. They are simple to prepare from easily available starting materials.

As development of the materials of the invention does not require pH values as high as prior art materials, there are advantages from the standpoint of replenishment rates, disposal of exhausted solutions, and corrosion resistance of the development apparatus.

The preferred field of use for materials of the invention is reprography, especially the preparation of halftone images from continuous tone images by conventional or electronic methods, the reproduction of line images and photomasks for printed circuits or other products of photofabrication, and the preparation of printing masters by phototypesetting. The aryl hydrazides of the invention can be used preferably with light-sensitive silver halides.

Although the invention is directed towards photographic silver halide materials containing aryl hydrazides, it does not exclude processes in which aryl hydrazides are also contained in the developer solution.

EXAMPLE 1

Preparation of 1-(p-tolyl)-5-(methylpyridinium-3-yl) semioxamazide tosylate (Compound II-56)

A. 1-methyl-3-methoxalylamidopyridinium tosylate 12.26 g (0.1 mole) oxalic acid methyl ester chloride dissolved in 100 ml THF were mixed slowly with stirring and ice bath cooling with a solution of 9.42 grams (0.1 mole) 3-amino-pyridine in 150 ml THF. A white solid precipitated immediately. After the end of the addition, stirring was continued one hour and the mixture was brought to room temperature. 18.2 ml of a 5.5 molar methanol solution of sodium methanolate were added. After the addition, the mixture was refluxed two hours and filtered from the precipitated salt. To alkylate the intermediate product, 3-methoxalylamino pyridine, the filtrate was mixed with 28 grams of the methyl ester of p-toluene sulfonic acid and refluxed eight hours. The reaction mixture was let stand overnight at room temperature and a bulky crystalline sludge separated. The precipitated solid was separated by filtration, washed with acetone, and dried. 26.5 grams (about 72% of theoretical) 1-methyl-3-methoxalylamidopyridinium tosylate were obtained and used without further purification.

B. 1-(p-tolyl)-5-(methylpyridinium-3-yl)-semioxamazide tosylate 7.95 grams (0.05 mole) tolyl hydrazine hydrochloride dissolved in 50 ml methanol were converted into the free base with sodium methanolate. The byproduct salt was filtered out and 18.5 grams (about 0.05 mole) 1-methyl-3-methoxalylamido- pyridinium tosylate dissolved in 50 ml methanol were added to the filtrate. The solution was heated under reflux 16 hours and let stand in the refrigerator. A yellow crystalline powder precipitated, was filtered out, and washed with ether. A second fraction of the yellow crystalline powder was recovered by adding ether to the filtrate from the reaction solution, isolated, and combined with the first fraction. The product thus obtained was recrystallized from methanol. 9 grams (about 40%) 1-(p-tolyl)-5- (methylpyridinium-3-yl)-semioxamazide tosylate were obtained as a yellow powder (solidification temperature 200°–203° C.).

In the use examples, the following prior art comparison compounds were used:

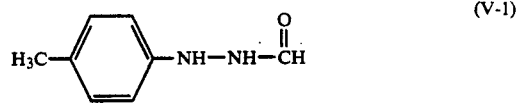
(V-1)

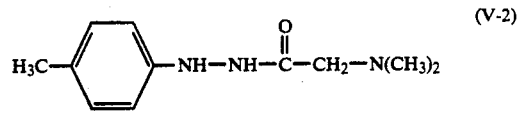
(V-2)

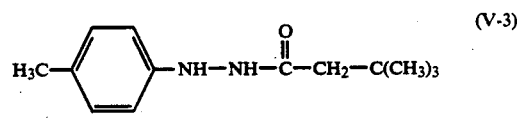
(V-3)

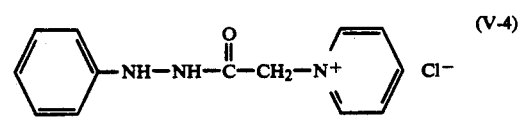
(V-4)

The quantities given for the materials of the invention and the comparison substances are always expressed in mmols per mol silver as silver halide.

EXAMPLE 2

(Use Example)

A silver bromide emulsion with cubic grains of 0.25 μm average edge length was prepared by pAg-controlled, double jet precipitation. The emulsion was washed and sensitized in the presence of 0.16 mmole sodium thiosulfate per mole silver halide. The usual quantities of antifoggants benzotriazole and 5-nitroindazole, a sensitizing dye for the green spectral region, $2.3 \times 10^{-3}$ mole potassium iodide per mole silver, an acrylic polymer dispersion, and conventional coating aids were added. The emulsion contained 80 g gelatin per mole silver.

Equal portions of this basic emulsion were mixed with ethanol solutions of the compounds listed in Table 1 and coated on a polyethylene terephthalate support provided with an antihalation layer. Simultaneously, a gelatin protective layer (1 g/m² dry weight), also containing a hardening agent, was applied. The resulting test films contained 4.4 g silver per m². The film samples were exposed with white light through and in contact with a master transparency consisting of one continuous tone wedge and one continuous tone wedge with an underlying contact screen. The samples were processed in a developing machine (Duerr Graphica) for 30 seconds at 38° C. with Kodak Ultratec Developer whose pH had been adjusted to 10.8 beforehand by the addition of sulfuric acid.

The following evaluation criteria were measured on the processed film samples:
  Density of fog and base—Dmin
  Maximum density—Dmax
  Relative sensitivity—S [as $-10 \times \log (I \times t)$ at density 3.0]
  Contrast between densities 1.0 and 3.0—Gamma
  Dot quality—DQ (from 1 for worst to 10 for best)

The results are summarized in Table 1. This shows that the invention's compounds yield ultrahigh contrast and good dot quality even at pH values below 11.

TABLE 1

| Sample No. | Compound No. | Quantity | Dmin | Dmax | S | Gamma | DQ |
|---|---|---|---|---|---|---|---|
| 1 | No additive | | 0.04 | 4.20 | 4.0 | 4.5 | 4 |
| 2 | V-1 | 2 | 0.04 | 4.10 | 5.7 | 5.3 | 4 |
| 3 | V-1 | 4 | 0.05 | 4.80 | 6.8 | 6.1 | 4 |
| 4 | V-1 | 8 | 0.05 | 4.60 | 8.1 | 7.4 | 4 |
| 5 | V-2 | 4 | 0.04 | 4.4 | 4.5 | 5.4 | 4 |
| 6 | V-2 | 8 | 0.05 | 4.4 | 4.7 | 6.0 | 4 |
| 7 | V-3 | 4 | 0.04 | 4.10 | 3.90 | 4.7 | 4 |
| 8 | V-3 | 8 | 0.04 | 4.20 | 3.80 | 4.7 | 4 |
| 9 | V-4 | 0.65 | 0.05 | 4.9 | 7.0 | 5.8 | 4 |
| 10 | V-4 | 1.30 | 0.05 | 5.0 | 8.0 | 6.5 | 4 |
| 11 | V-4 | 4.0 | 0.06 | 5.0 | 9.3 | 8.2 | 4 |
| 12 | II-1 | 0.65 | 0.04 | 4.9 | 9.4 | 18 | 9–10 |
| 13 | II-2 | 0.65 | 0.04 | 4.9 | 9.4 | 17 | 9–10 |
| 14 | II-3 | 0.65 | 0.04 | 5.1 | 10.0 | 20 | 10 |
| 15 | II-7 | 1.3 | 0.04 | 5.1 | 9.2 | 14 | 8–9 |
| 16 | II-8 | 1.3 | 0.04 | 4.7 | 9.0 | 14 | 8–9 |
| 17 | II-31 | 1.3 | 0.04 | 4.8 | 9.2 | 16 | 10 |
| 18 | II-39 | 0.65 | 0.04 | 5.2 | 11.5 | 23 | 10 |
| 19 | II-40 | 0.65 | 0.4 | 5.2 | 11.3 | 21 | 10 |
| 20 | II-33 | 1.3 | 0.04 | 4.7 | 9.8 | 12 | 9 |
| 21 | II-47 | 0.65 | 0.05 | 5.0 | 11.4 | 20 | 7 |
| 22 | II-52 | 0.65 | 0.06 | 4.8 | 8.5 | 10 | 8 |
| 23 | II-53 | 2.0 | 0.05 | 4.7 | 8.8 | 14 | 7 |
| 24 | II-56 | 1.3 | 0.05 | 5.0 | 9.6 | 18 | 7 |

EXAMPLE 3

A cubic grain silver bromide emulsion was prepared and sensitized as described in Example 2. The usual quantities of benzotriazole as an antifoggant, a sensitizing dye for the green spectral region, $2.3 \times 10^{-3}$ moles potassium iodide per mole silver, a polyethylene dispersion, and conventional coating aids were added. The emulsion contained 80 grams gelatin per mole silver. Equal portions of this emulsion were mixed with ethanol solutions of the compounds listed in Table 2. Test films were prepared from the emulsions as described in Example 2.

Samples of these films were exposed as described in Example 2 and developed in a developing machine with a developer of the following composition at 36° C for 40 seconds.

| Developer Formulation: | Additions in grams/liter |
|---|---|
| Water | 600 |
| KOH | 30 |
| $K_2S_2O_5$ | 66 |
| EDTA | 3 |
| $Na_2CO_3 \cdot H_2O$ | 48 |
| KBr | 3 |
| Benzotriazole | 0.5 |
| Phenyl mercaptotetrazole | 0.05 |
| Hydroquinone | 25 |
| N-methyl-p-aminophenol sulfate | 1.5 |
| Diethylamino propanediol | 25 |
| Water to make | 1 liter |
| pH | 10.9 at 20° C. |

The evaluation was conducted for the sensitometric criteria cited in Example 2; however, dot quality was determined visually in the screened wedge for three different dot sizes at 80x enlargement. The following ranges were selected for the determination:

| Highlights: | at 95% |
| Midrange tones: | at 50% |
| Shadows: | at 10% |

The judgment criteria were the contour sharpness and edge sharpness of the dots and the interdot fog, which is particularly visible in the highlights.

The results are compiled in Table 2.

The results show again that ultrahigh contrast and good dot quality were achieved at very low concentration of the compounds of the invention, even at low pH values.

TABLE 2

| Sample No. | Compound No. | Quantity | Dmin | Dmax | S | Gamma | DQ 10% | DQ 50% | DQ 90% |
|---|---|---|---|---|---|---|---|---|---|
| 1 | II-3 | 1.2 | 0.05 | 5.2 | 10.2 | 16 | 9 | 8–9 | 6 |
| 2 | II-14 | 0.4 | 0.05 | 5.3 | 10.8 | 20 | 10 | 10 | 7–8 |
| 3 | II-15 | 0.4 | 0.04 | 5.2 | 10.8 | 18 | 10 | 10 | 8 |
| 4 | II-16 | 0.4 | 0.04 | 5.3 | 10.7 | 18 | 10 | 10 | 7 |
| 5 | II-21 | 0.4 | 0.05 | 5.0 | 9.7 | 12 | 9 | 9 | 7 |
| 6 | II-22 | 0.4 | 0.05 | 5.2 | 10.0 | 14 | 9 | 9–10 | 7–8 |
| 7 | II-27 | 0.4 | 0.04 | 5.4 | 10.9 | 23 | 10 | 10 | 9 |
| 8 | II-24 | 0.4 | 0.04 | 5.4 | 10.8 | 24 | 10 | 10 | 8 |
| 9 | II-25 | 0.4 | 0.04 | 5.0 | 9.0 | 12 | 9 | 9–10 | 7 |
| 10 | II-25 | 0.9 | 0.04 | 5.0 | 9.5 | 22 | 10 | 10 | 8 |
| 11 | II-26 | 0.4 | 0.05 | 5.1 | 9.2 | 12 | 9 | 9 | 7 |
| 12 | II-26 | 0.6 | 0.04 | 5.1 | 9.4 | 20 | 10 | 10 | 9 |
| 13 | II-28 | 0.4 | 0.04 | 5.2 | 10.0 | 15 | 10 | 10 | 7–8 |

TABLE 2-continued

| Sample No. | Compound No. | Quantity | Dmin | Dmax | S | Gamma | DQ 10% | DQ 50% | DQ 90% |
|---|---|---|---|---|---|---|---|---|---|
| 14 | II-29 | 1.2 | 0.04 | 5.0 | 9.5 | 18 | 9 | 9 | 7 |
| 15 | II-34 | 0.6 | 0.05 | 5.0 | 7.0 | 20 | 9 | 8–9 | 6 |
| 16 | II-39 | 0.4 | 0.04 | 5.3 | 10.8 | 25 | 10 | 10 | 9 |
| 17 | II-40 | 0.4 | 0.04 | 5.2 | 10.7 | 22 | 10 | 10 | 9 |
| 18 | II-41 | 0.4 | 0.04 | 5.3 | 10.2 | 22 | 10 | 10 | 9 |
| 19 | II-43 | 0.4 | 0.04 | 5.2 | 11.1 | 20 | 10 | 10 | 9 |
| 20 | II-44 | 0.4 | 0.04 | 5.2 | 9.3 | 20 | 10 | 10 | 9 |
| 21 | II-57 | 0.4 | 0.04 | 5.0 | 8.0 | 8 | 8 | 8 | 6 |
| 22 | II-35 | 0.6 | 0.05 | 5.0 | 7.8 | 15 | 9 | 8–9 | 6 |
| 23 | V-4 | 3.6 | 0.05 | 4.6 | 7.0 | 5.0 | 3 | 4 | 3 |
| 24 | No additive | | 0.04 | 4.3 | 4.5 | 4.8 | 3 | 4 | 3 |

What is claimed is:

1. A photographic material containing an aryl hydrazide for the production of images with ultrahigh contrast comprising a support having thereon at least one silver halide emulsion layer, the emulsion, or at least one another auxiliary layer in contact with the silver halide emulsion layer on said support contains a compound of Formula (I)

$$Ar-NR-NR_1-G-X^+A^-  \quad (I)$$

wherein Ar is a substituted phenyl group or another substituted or unsubstituted aryl group, G is the group CO, SO, SO$_2$, phosphonyl, phosphoryl or C=NR$_2$, X$^+$ is a radical containing a cationic group with a quaternary nitrogen atom, R, R$_1$, and R$_2$, which can be the same or different, are hydrogen, alkyl or alkyl sulfinyl groups with one to six carbon atoms, and A$^-$ is an anion, the improvement wherein the quaternary nitrogen atom is included in a substituted or unsubstituted imidazolium, imidazolinium, isoquinolinium, or quinolinium group.

2. The photographic silver halide material according to claim 1, wherein the aryl hydrazide is of the Formula (II):

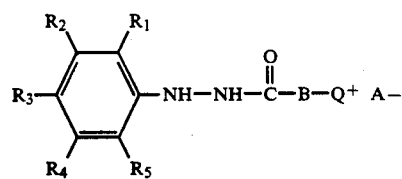

wherein R$_1$ to R$_5$ are radicals which can be the same or different, at least one of which is not hydrogen, and which are represented by hydrogen, halogen, alkyl, alkoxy, hydroxyalkyl, halogenated alkyl, alkyl amino, aliphatic acylamino, with, in each case, one to 20 carbon atoms, cycloalkyl with 5 to 7 carbon atoms, aryl, aryloxy, or aromatic acylamino with, in each case, six to ten carbon atoms, aralkyl or aralkoxy with one to three carbon atoms in the alkylene chain, an aliphatic acyl amino radical with one to four carbon atoms and substituted with a phenoxy radical optionally substituted with one or more alkyl radicals with one to ten carbon atoms, a five-member or six-member heterocyclic ring with nitrogen and/or sulfur as heteroatoms, which ring can also be condensed on a benzene ring, or an alkyl or phenyl sulfonamido radical, whereby, in place of two substituents, a saturated or unsaturated ring can also be condensed onto the compounds, Q$^+$ is 3-alkyl or 3-alkenyl imidazole-1-yl, optionally substituted further, quinolyl or isoquinolyl optionally substituted, whereby the substituents can be alkyl, alkenyl, aminoalkyl, hydroxyalkyl radicals, benzyl, phenyl, phenylmethyl or pyridyl radicals, carboxyl, carbamide, carboxyalkyl, cycloalkyl thioureimido methyl or hydroxy groups, trialkylammonium ethyl groups, amino, monoalkylamino and dialkylamino groups, N-piperidino groups, N-pyrrolidino groups or also chlorine, the heterocyclic ring can be condensed to a benzene ring, and whereby all alkyl groups of a radical Q$^+$ can be the same or different and/or can be substituted with hydroxyl or sulfonic acid groups, each alkyl group having, however, 12 carbon atoms at most, B is a bridge that can contain one to three methylene groups, an oxygen atom, and —CO—NH— or —N-H—groups, or, if it is not directly attached to a quaternary nitrogen, can also consist of a simple bond, whereby the methylene groups and —NH— groups themselves can be substituted with methyl or ethyl groups, A$^-$ is an anion that is omitted if Q$^+$ contains a sulfo group or a carboxyl group.

3. The photographic silver halide material according to claim 2 wherein the aryl hydrazide of Formula (II) contained therein is substituted on one of the radicals R$_1$ to R$_5$ or Q$^+$ with a radical of the formula R$_6$—X—C-S—X'—, whereby one of the groups X and X' is represented by NR$_7$ and the other by NR$_8$, —O— or —S—, and R$_6$, R$_7$, and R$_8$ are represented by hydrogen and alkyl, cycloalkyl, or aryl groups with up to eight carbon atoms.

* * * * *